US00PP14692P29

(12) United States Plant Patent
Shiozaki

(10) Patent No.: US PP14,692 P2
(45) Date of Patent: Apr. 13, 2004

(54) VARIETY OF DICENTRA PLANT NAMED 'CANDY HEARTS'

(50) Latin Name: *Dicentra peregrina×eximia*
Varietal Denomination: Candy Hearts

(75) Inventor: Akira Shiozaki, Fukagawa (JP)

(73) Assignee: Walter Blom & Zoon B.V., Holland (NL)

( * ) Notice: Subject to any disclaimer, the term of this patent is extended or adjusted under 35 U.S.C. 154(b) by 0 days.

(21) Appl. No.: 10/417,033

(22) Filed: Apr. 16, 2003

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—Anne Marie Grunberg
(74) *Attorney, Agent, or Firm*—Webb Ziesenheim Logsdon Orkin & Hanson, P.C.

(57) ABSTRACT

A new and distinct *Dicentra peregrina×eximia* plant with a compact habit and long flowering period.

3 Drawing Sheets

Botanical classification: *Dicentra peregrina×eximia.*
Varietal denomination: 'Candy Hearts'.

BACKGROUND OF THE INVENTION

The present invention comprises a new and distinct cultivar of *Dicentra peregrina×eximia* known by the varietal name 'Candy Hearts'. The new variety was discovered in Hokkaido, Japan on May 20, 1990. The first date of asexual reproduction by cuttings was in February of 1991 in Hokkaido, Japan. The new variety is the result of a planned breeding program cross between unpatented, unnamed *Dicentra peregrina rubra* (female parent) and *Dicentra eximia* (male parent). The new variety exhibits similar form and foliage to both parents, but has a more improved vigor and a longer flowering period than both parents. The new variety exhibits similar flower color to an unpatented variety of *Dicentra eximia*, but has more vigor and a different growth habit. The new variety has been trial and field tested and has been found to retain its distinctive characteristics and remain true to type through successive propagations. The following characteristics distinguish 'Candy Hearts' from other varieties:

1. Plant size;
2. Improved vigor;
3. High flower count; and
4. Long flowering period.

DESCRIPTION OF THE DRAWINGS

The accompanying photographic drawings illustrate the new variety, with the color being as nearly true as is possible with color illustrations of this type.

DESCRIPTION OF THE PLANT

Figure 1:
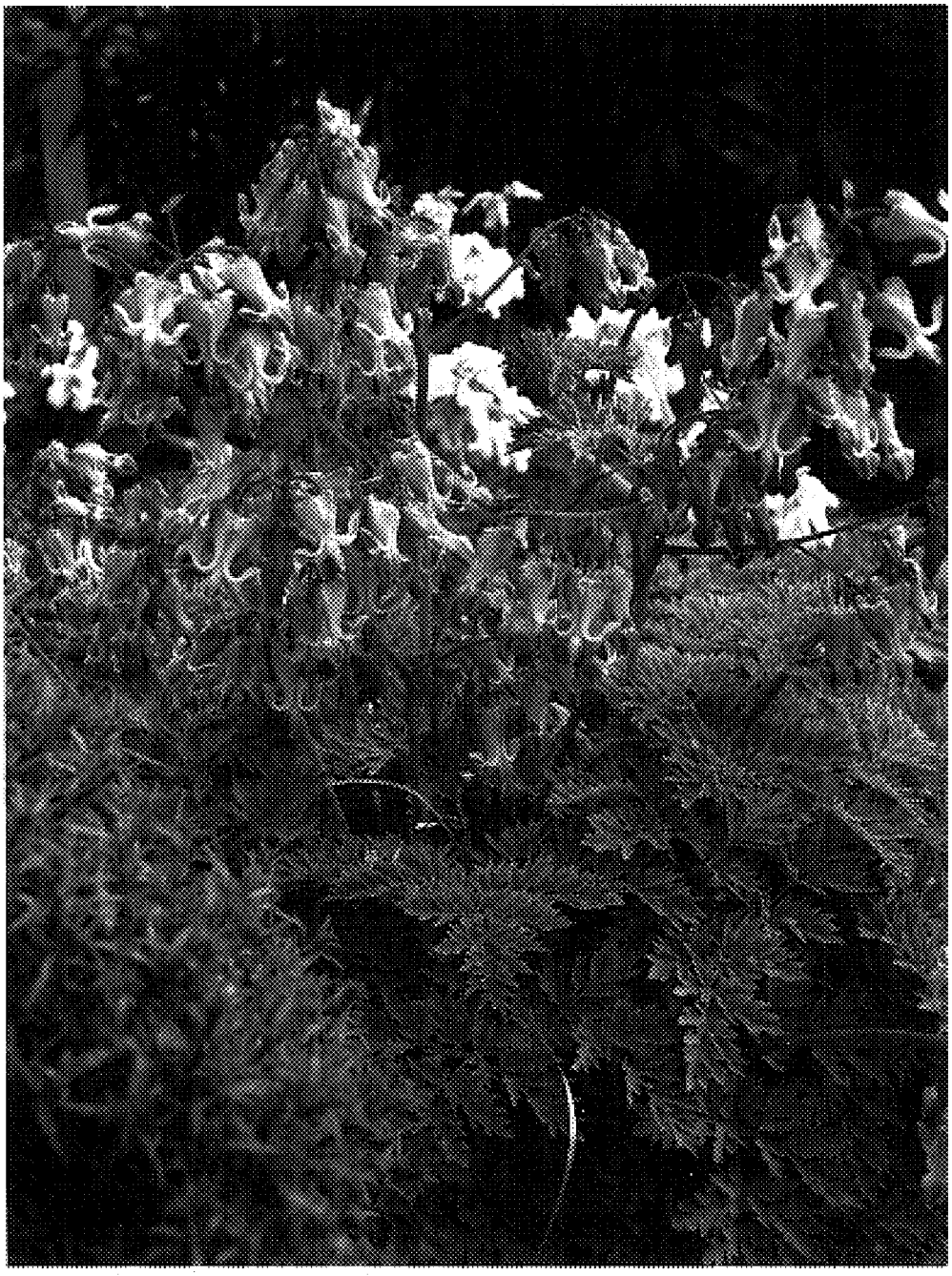
FIG. 1 is a photograph of the plant.
Figure 2:
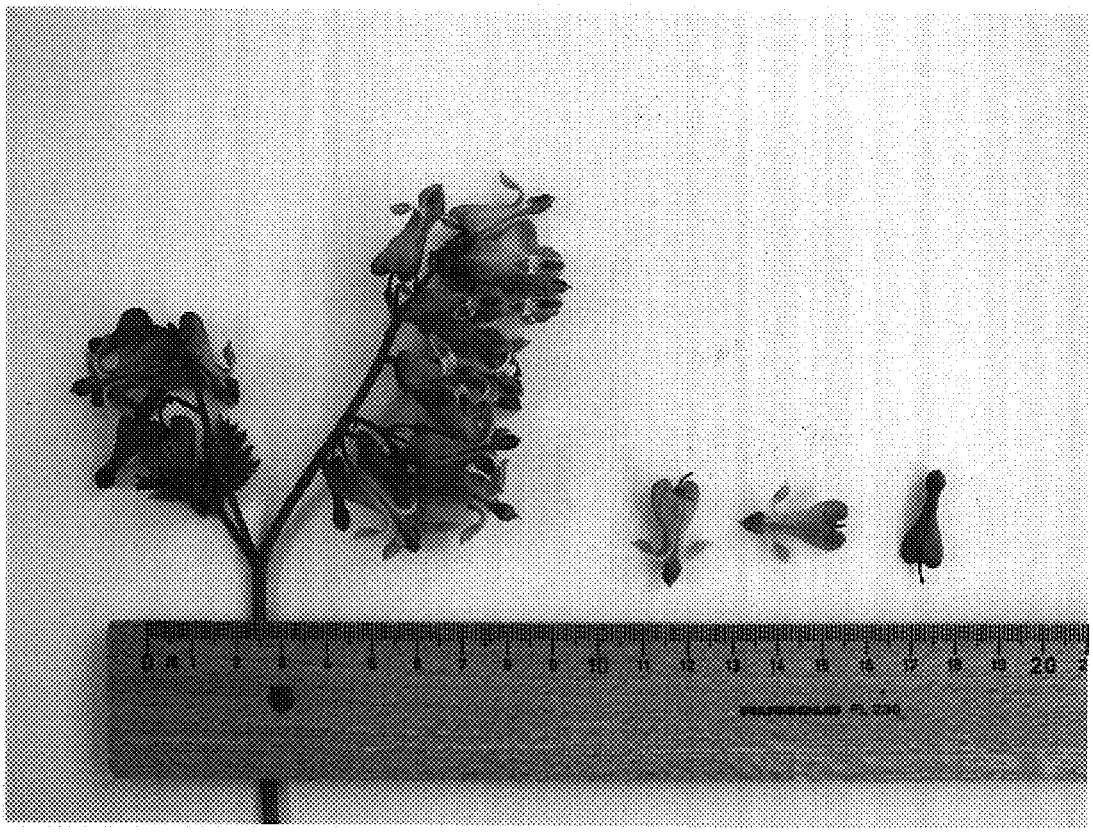
FIG. 2 is a close up view of the blossoms of the new plant.
Figure 3:
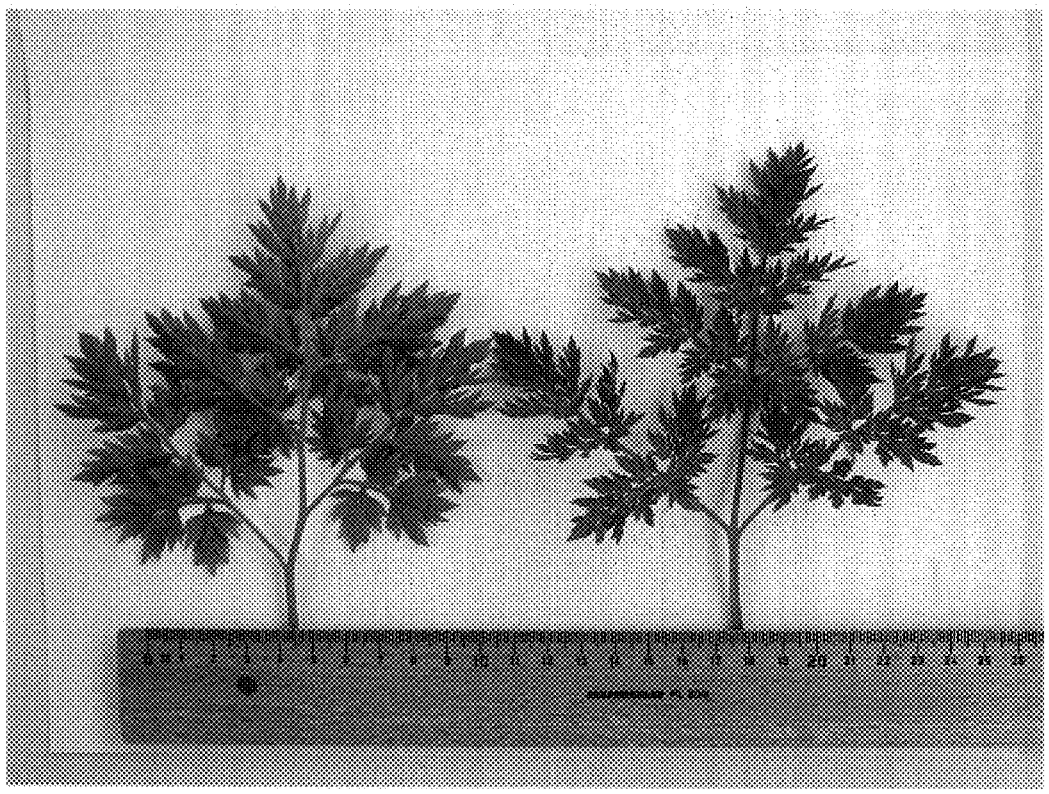
FIG. 3 is a close up view of the foliage of the new plant.

The following detailed description sets forth the characteristics of the new cultivar grown outside in the open ground with no extra fertilizer in The Netherlands. The data which defines these characteristics were collected by asexual reproductions by cuttings. The color readings were taken in The Netherlands in natural daylight. Color references are primarily to The R.H.S. Colour Chart of The Royal Horticultural Society of London.

PLANT

Time to initiate roots: About 21 days at 15° C.
Time to develop roots: About 49 days at 15° C.
Time to produce a finished flowering plant from a rooted cutting: About 10–12 weeks in a 12 cm container.
Rooting habit: Fine, rhizomatous root system.
Form: Low, spreading, mounded foliage.
Stem: Not present. Foliage and flowers arise directly from root system.
Height: 25–30 cm.
Diameter: 30–35 cm.
Vigor: Good.
Branching habit: Non-branching.
Foliage:

*Arrangement.*—Petioles arise from base of plant bearing deeply cut bipinnate foliage.
*Size of leaf.*—Length: 10–12 cm. Width: 12–15 cm.
*Leaflets.*—Shape (generally): Rounded, but deeply cut. Number: 5–7. Width: 5–6 cm. Length: 6–9 cm. Shape of apex: Acute. Shape of base: Uneven. Aspect: Horizontally held; Drooping at tip. Texture: Smooth. Margin type: Deeply cut. Pubescence: Upper surface: Glabrous. Lower surface: Glabrous. Color: Young leaflet: Upper surface: Between 126D and 128B. Lower surface: Between 126D and 128B. Mature leaflet: Upper surface: Between 126C, 126D. Lower surface: Between 127C and 127D.
*Petiole.*—Length: 9–14 cm. Diameter: 4–5 mm. Color: Between 144A and 144B.

FLOWER

Bud:

*Stage when bud characteristics determined.*—Just before opening.
*Shape.*—Pitcher-shaped.
*Diameter.*—9–10 mm.
*Length.*—21–23 mm.
*Color.*—Between 57B and 57C.

Natural flowering season: March until October, depending on weather conditions.

Panicle:

*Shape.*—Elongated, branched panicle.

*Number of flowers.*—Between 12–18.

*Length of pedicle.*—Between 5–7 mm.

*Length of peduncle.*—Between 2–5 cm.

Corolla:

*Form.*—Zygomorphic; fused petals (lobed).

*Petals.*—Total number: 4 in 2 pairs. Outer pair: Number: 1. Length: 18–20 mm. Width: Between 2 mm and 5 mm. Shape: Fused; cordate. Aspect: Pendant. Margin: Entire. Texture: Smooth. Color When opening: Upper surface: Between 57B and 57C. Lower surface: 69C. Fully opened: Upper surface: Between 57B and 57C. Lower surface: Between 75B and 75C.

*Inner pair.*—Number: 1. Length: 20–22 mm. Width: 4–5 mm across pair. Shape: Fused tube. Aspect: Pendant; hanging. Margin: Entire. Texture: Smooth. Color When opening: Upper surface: Between 57B and 57C. Lower surface: 69C. Fully opened: Upper surface: Between 57C and 57D. Lower surface: Between 75B and 75C.

Calyx:

*Form.*—Vestigial in two halves.

*Length.*—2–3 mm.

*Diameter.*—2 mm.

*Sepal shape.*—Acute.

*Sepal margin.*—Entire.

*Sepal texture.*—Smooth.

*Sepal size.*—Length: 2–3 mm. Width: 2 mm.

*Sepal color.*—Upper surface: 55A. Lower surface: 64B.

Fragrance: None.

Disease resistance: Good.

Temperature tolerance: Between −10° C. to 30° C.

Lasting quality: Excellent; lasting over 3 weeks depending on the weather.

REPRODUCTIVE ORGANS

Stamens:

*Number.*—2 per flower.

*Filaments.*—Filament length: Approximately 10 mm. Color: 69B, with shading of 57B.

*Anthers.*—Shape: Oval. Length: 2 mm. Color: 69B, with veins of 57B.

*Pollen.*—Color: 22A. Amount: Minimal.

Pistils:

*Length.*—Approximately 10 mm.

*Style.*—Length: 8–9 mm. Color: 138C.

*Stigma.*—Shape: Rounded. Color: 153A.

Seed/fruit production: None observed.

I claim:

1. A new and distinct variety of *Dicentra peregrina*× *eximia* plant substantially as shown and described.

* * * * *